United States Patent
Smith et al.

(10) Patent No.: US 11,406,332 B2
(45) Date of Patent: *Aug. 9, 2022

(54) SYSTEM AND METHOD FOR DUAL ENERGY AND/OR CONTRAST ENHANCED BREAST IMAGING FOR SCREENING, DIAGNOSIS AND BIOPSY

(71) Applicant: Hologic, Inc., Marlborough, MA (US)

(72) Inventors: Andrew P. Smith, Lexington, MA (US); Jay A. Stein, Boston, MA (US); Zhenxue Jing, Chadds Ford, PA (US); Baorui Ren, Andover, MA (US); Loren Niklason, N Tetonia, ID (US); Christopher Ruth, Boxford, MA (US); Ian Shaw, Yorktown Heights, NY (US)

(73) Assignee: Hologic, Inc., Marlborough, MA (US)

( * ) Notice: Subject to any disclaimer, the term of this patent is extended or adjusted under 35 U.S.C. 154(b) by 355 days.

This patent is subject to a terminal disclaimer.

(21) Appl. No.: 16/439,131

(22) Filed: Jun. 12, 2019

(65) Prior Publication Data

US 2019/0290221 A1  Sep. 26, 2019

Related U.S. Application Data

(63) Continuation of application No. 14/695,090, filed on Apr. 24, 2015, now Pat. No. 10,357,211, which is a
(Continued)

(51) Int. Cl.
*A61B 6/02* (2006.01)
*A61B 6/00* (2006.01)

(52) U.S. Cl.
CPC .............. *A61B 6/025* (2013.01); *A61B 6/463* (2013.01); *A61B 6/481* (2013.01); *A61B 6/482* (2013.01);
(Continued)

(58) Field of Classification Search
CPC ........... A61B 10/04; A61B 6/025; A61B 6/12; A61B 6/4035; A61B 6/4417; A61B 6/463;
(Continued)

(56) References Cited

U.S. PATENT DOCUMENTS

| 3,502,878 A | 3/1970 | Stewart |
| 3,863,073 A | 1/1975 | Wagner |

(Continued)

FOREIGN PATENT DOCUMENTS

| AU | 2014339982 | 4/2015 |
| CN | 1846622 | 10/2006 |

(Continued)

OTHER PUBLICATIONS

"Filtered Back Projection", (NYGREN), published May 8, 2007, URL: http://web.archive.org/web/19991010131715/http://www.owlnet.rice.edu/~elec539/Projects97/cult/node2.html, 2 pgs.
(Continued)

*Primary Examiner* — Amelie R Davis
(74) *Attorney, Agent, or Firm* — Merchant & Gould P.C.

(57) ABSTRACT

Systems and methods for x-ray imaging a patient's breast in combinations of dual-energy, single-energy, mammography and tomosynthesis modes that facilitate screening for and diagnosis of breast abnormalities, particularly breast abnormalities characterized by abnormal vascularity.

16 Claims, 10 Drawing Sheets

Related U.S. Application Data continuation of application No. 13/415,675, filed on Mar. 8, 2012, now Pat. No. 9,020,579.

(60) Provisional application No. 61/450,304, filed on Mar. 8, 2011.

(52) U.S. Cl.
CPC ............ *A61B 6/502* (2013.01); *A61B 6/5235* (2013.01); *A61B 6/4035* (2013.01)

(58) Field of Classification Search
CPC ......... A61B 6/466; A61B 6/481; A61B 6/482; A61B 6/502; A61B 6/5235
See application file for complete search history.

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,641 A | 12/1985 | Caugant et al. |
| 4,706,269 A | 11/1987 | Reina et al. |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,668,889 A | 9/1997 | Hara |
| 5,671,288 A | 9/1997 | Wilhelm et al. |
| 5,712,890 A | 1/1998 | Spivey |
| 5,719,952 A | 2/1998 | Rooks |
| 5,735,264 A | 4/1998 | Siczek et al. |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 * | 1/2004 | Zhao ................. A61B 6/032 378/37 |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,554 B2 | 2/2006 | Mertelmeier |

(56) References Cited

U.S. PATENT DOCUMENTS

| | | |
|---|---|---|
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,606,801 B2 | 10/2009 | Faitelson et al. |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 | 4/2010 | Ren et al. |
| 7,705,830 B2 | 4/2010 | Westerman et al. |
| 7,760,924 B2 | 7/2010 | Ruth et al. |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | Defreitas et al. |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0155209 A1 | 6/2006 | Miller et al. |
| 2006/0147099 A1 | 7/2006 | Marshall et al. |
| 2006/0197753 A1 | 9/2006 | Hotelling |
| 2006/0210131 A1 | 9/2006 | Wheeler |

(56) References Cited

U.S. PATENT DOCUMENTS

| | | |
|---|---|---|
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0291618 A1 | 12/2006 | Eberhard et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | Defreitas et al. |
| 2009/0005668 A1 | 1/2009 | West et al. |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1* | 2/2010 | Yu .................. A61B 6/025 378/20 |
| 2010/0049046 A1 | 2/2010 | Peiffer |
| 2010/0054400 A1 | 3/2010 | Ren et al. |
| 2010/0079405 A1 | 4/2010 | Bernstein |
| 2010/0086188 A1 | 4/2010 | Ruth et al. |
| 2010/0088346 A1 | 4/2010 | Urness et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166267 A1 | 7/2010 | Zhang |
| 2010/0195882 A1 | 8/2010 | Ren et al. |
| 2010/0208037 A1 | 8/2010 | Sendai |
| 2010/0231522 A1 | 9/2010 | Li |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110576 A1 | 5/2011 | Kreeger |
| 2011/0150447 A1 | 6/2011 | Li |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014504 A1 | 1/2012 | Jang |
| 2012/0014578 A1 | 1/2012 | Karssemeijer |
| 2012/0069951 A1 | 3/2012 | Toba |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0189092 A1 | 7/2012 | Jerebko |
| 2012/0194425 A1 | 8/2012 | Buelow |
| 2012/0238870 A1 | 9/2012 | Smith et al. |
| 2012/0293511 A1 | 11/2012 | Mertelmeier |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2014/0033126 A1 | 1/2014 | Kreeger |
| 2014/0035811 A1 | 2/2014 | Guehring |
| 2014/0064444 A1 | 3/2014 | Oh |
| 2014/0073913 A1 | 3/2014 | DeFreitas et al. |
| 2014/0219534 A1 | 8/2014 | Wiemker et al. |
| 2014/0219548 A1 | 8/2014 | Wels |
| 2014/0327702 A1 | 11/2014 | Kreeger et al. |
| 2014/0328517 A1 | 11/2014 | Gluncic |
| 2015/0052471 A1 | 2/2015 | Chen |
| 2015/0061582 A1 | 4/2015 | Smith |
| 2015/0238148 A1 | 8/2015 | Georgescu |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman |
| 2016/0228034 A1 | 8/2016 | Gluncic |
| 2016/0235380 A1 | 8/2016 | Smith |
| 2016/0367210 A1 | 12/2016 | Gkanatsios |
| 2017/0071562 A1 | 3/2017 | Suzuki |
| 2017/0262737 A1 | 9/2017 | Rabinovich |
| 2018/0047211 A1 | 2/2018 | Chen et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0015173 A1 | 1/2019 | DeFreitas |
| 2019/0043456 A1 | 2/2019 | Kreeger |
| 2020/0046303 A1 | 2/2020 | DeFreitas |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |

(56) References Cited

U.S. PATENT DOCUMENTS

| | | |
|---|---|---|
| 2020/0345320 A1 | 11/2020 | Chen |
| 2021/0100518 A1 | 4/2021 | Chui |
| 2021/0113167 A1 | 4/2021 | Chui |
| 2021/0118199 A1 | 4/2021 | Chui |
| 2022/0005277 A1 | 1/2022 | Chen |
| 2022/0013089 A1 | 1/2022 | Kreeger |

FOREIGN PATENT DOCUMENTS

| | | |
|---|---|---|
| CN | 202161328 | 3/2012 |
| CN | 102429678 | 5/2012 |
| CN | 107440730 | 12/2017 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 3060132 | 4/2019 |
| JP | H09-198490 | 7/1997 |
| JP | H09-238934 | 9/1997 |
| JP | H10-33523 | 2/1998 |
| JP | 2000-200340 | 7/2000 |
| JP | 2002-282248 | 10/2002 |
| JP | 2003-189179 | 7/2003 |
| JP | 2003-199737 | 7/2003 |
| JP | 2003-531516 | 10/2003 |
| JP | 2006-519634 | 8/2006 |
| JP | 2006-312026 | 11/2006 |
| JP | 2007-130487 | 5/2007 |
| JP | 2007-330334 | 12/2007 |
| JP | 2007-536968 | 12/2007 |
| JP | 2008-068032 | 3/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2012/501750 | 1/2012 |
| JP | 2012011255 | 1/2012 |
| JP | 2012-061196 | 3/2012 |
| JP | 2013-244211 | 12/2013 |
| JP | 2014-507250 | 3/2014 |
| JP | 2014-534042 | 12/2014 |
| JP | 2015-506794 | 3/2015 |
| JP | 2016-198197 | 12/2015 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 2005051197 | 6/2005 |
| WO | 2005/110230 | 11/2005 |
| WO | 2005110230 | 11/2005 |
| WO | 2005/112767 | 12/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2014/149554 | 9/2014 |
| WO | 2014/207080 | 12/2014 |
| WO | 2015/061582 | 4/2015 |
| WO | 2015/066650 | 5/2015 |
| WO | 2015/130916 | 9/2015 |
| WO | 2016/103094 | 6/2016 |
| WO | 2016/184746 | 11/2016 |
| WO | 2018/183548 | 10/2018 |
| WO | 2018/183549 | 10/2018 |
| WO | 2018/183550 | 10/2018 |
| WO | 2018/236565 | 12/2018 |

OTHER PUBLICATIONS

Canadian Office Action in Application 2829349, dated Oct. 15, 2018, 4 pages.
Chinese 2nd Office Action in Application 201480058064.5, dated Jul. 16, 2019, 5 pgs.
European Communication in Application 10707751.3, dated Oct. 4, 2018, 5 pages.
European Communication in Application 10707751.3, dated Aug. 7, 2019, 6 pages.
European Extended Search Report for European Patent Application No. 14770362.3 dated Sep. 28, 2016, 8 pgs.
European Extended Search Report in Application 14855181.5, dated May 15, 2017, 7 pages.
European extended Search Report in Application 18153706.9, dated Jun. 1, 2018, 8 pages.
European Mar. 23, 2009 European Search Report in connection with counterpart European patent Application No. 077750818.
European Office Action in Application 10707751.3, dated Feb. 19, 2018, 5 pgs.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
Japanese Notice of Final Rejection in Application 2016-526115, dated Jun. 24, 2019, 5 pages.
Observations by Third Party, Remarks concerning European patent application No. 10707751.3 according to Article 115 EPC, dated Apr. 24, 2014, 8 pgs.
PCT Feb. 20, 2008 International Search Report and Written Opinion in connection with corresponding International patent application No. PCT/US2007/04006, 7 pgs.
PCT International Preliminary Report on Patentability in International Application PCT/US2014/061994, dated Apr. 26, 2016, 5 pages.
PCT International Search Report and Written Opinion in Application PCT/US2010/025873, dated Aug. 2, 2010, 19 pgs.
PCT International Search Report in Application PCT/US2014/026164, dated Jul. 28, 2014, 1 page.
PCT International Written Report for International Application PCT/US2014/026164, dated Jul. 28, 2014, 12 pgs.
PCT Written Opinion in International Application PCT/US2014/061994, dated Jan. 22, 2015, 4 pages.

(56) References Cited

OTHER PUBLICATIONS

Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Berg WA et al., "Combined screening with ultrasound and mammography vs mammography alone in women at elevated risk of breast cancer", JAMA 299:2151-2163, 2008.
Carton AK, et al., "Dual-energy contrast-enhanced digital breast tomosynthesis—a feasibility study", BR J Radiol. Apr. 2010;83(988):344-50.
Chen SC, et al., "Initial clinical experience with contrast-enhanced digital breast tomosynthesis", Acad Radio. Feb. 2007 14(2):229-38.
Diekmann F., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain C., et al., "Contrast-enhanced digital mammography", Eur J Radiol. 2009; 69:34-42.
EP Extended Search Report dated Jul. 18, 2014 in EP App 12754521.8.
Freiherr G., "Breast tomosynthesis trials show promise", Diagnostic Imaging—San Francisco 2005, V27; N4:42-48.
Giger, M. et al., An Intelligent Workstation for Computer-aided Diagnosis, RadioGraphics, (1993), 13(3): 657-656.
Giger, M. et al., Development of a smart workstation for use in mammography, Proceedings of SPIE, (1991), 45:101-103.
ICRP Publication 60: 1990 Recommendations of the International Commission on Radiological Protection.
Jochelson M., et al, Bilateral, RSNA 2010, 96th Scientific Assembly and Scientific Meeting.
Jong, RA, et al., Contrast-enhanced digital mammography: initial clinical experience. Radiology 2003; 228:842-850.
Kopans, et.al. Will tomosynthesis replace conventional mammography? Plenary Session SFN08: RSNA 2005.
Lehman CD, et al. MRI evaluation of the contralateral breast in women with recently diagnosed breast cancer. N Engl J Med 2007; 356:1295-1303.
Lewin JM, et al., Dual-energy contrast-enhanced digital subtraction mammography: feasibility. Radiology 2003; 229:261-268.
Lindfors KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
PCT/US12/28334 International Search Report and Written Opinion, dated Jul. 5, 2012.
Poplack SP, et al., Digital breast tomosynthesis: initial experience in 98 women with abnormal digital screening mammography. AJR Am J Roentgenology Sep. 2007 189(3):616-23.
Prionas ND, et al., Contrast-enhanced dedicated breast CT: initial clinical experience. Radiology. Sep. 2010 256(3):714-723.
Rafferty E. et al. Assessing Radiologist Performance Using Combined Full-Field Digital Mammography and Breast Tomosynthesis Versus Full-Field Digital Mammography Alone: Results . . . presented at 2007 Radiological Society of North America meeting, Chicago IL.
Smith, A., Full field breast tomosynthesis. Radiol Manage. Sep.-Oct. 2005; 27(5):25-31.
Weidner N, Semple JP, Welch WR, Folkman J. Tumor angiogenesis and metastasis: correlation in invasive breast carcinoma. New England Journal of Medicine 1991; 324:1-8.
Weidner N, The importance of tumor angiogenesis: the evidence continues to grow. Am J Clin Pathol. Nov. 2004 122(5):696-703.
"Supersonic to feature Aixplorer Ultimate at ECR", AuntiMinnie.com, 3 pages (Feb. 2018).

Burbank, Fred, "Stereotactic Breast Biopsy: Its History, Its Present, and Its Future", published in 1996 at the Southeastern Surgical Congress, 24 pages.
E. Shaw de Paredes et al., "Interventional Breast Procedure", published Sep./Oct. 1998 in Curr Probl Diagn Radiol, pp. 138-184.
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.
Dromain, Clarisse et al., "Dual-energy contrast-enhanced digital mammography: initial clinical results", European Radiology, Sep. 14, 2010, vol. 21, pp. 565-574.
Reynolds, April, "Stereotactic Breast Biopsy: A Review", Radiologic Technology, vol. 80, No. 5, Jun. 1, 2009, pp. 447M-464M, XP055790574.
Al Sallab et al., "Self Learning Machines Using Deep Networks", Soft Computing and Pattern Recognition (SoCPaR), 2011 Int'l. Conference of IEEE, Oct. 14, 2011, pp. 21-26.
Caroline, B.E. et al., "Computer aided detection of masses in digital breast tomosynthesis: A review", 2012 International Conference on Emerging Trends in Science, Engineering and Technology (INCOSET), Tiruchirappalli, 2012, pp. 186-191.
Chan, Heang-Ping et al., "ROC Study of the effect of stereoscopic imaging on assessment of breast lesions," Medical Physics, vol. 32, No. 4, Apr. 2005, 1001-1009.
EFilm Mobile HD by Merge Healthcare, web site: http://itunes.apple.com/bw/app/efilm-mobile-hd/id405261243?mt=8, accessed on Nov. 3, 2011 (2 pages).
EFilm Solutions, eFilm Workstation (tm) 3.4, website: http://estore.merge.com/na/estore/content.aspx?productID=405, accessed on Nov. 3, 2011 (2 pages).
Ertas, M. et al., "2D versus 3D total variation minimization in digital breast tomosynthesis", 2015 IEEE International Conference on Imaging Systems and Techniques (IST), Macau, 2015, pp. 1-4.
Ghiassi, M. et al., "A Dynamic Architecture for Artificial Networks", Neurocomputing, vol. 63, Aug. 20, 2004, pp. 397-413.
Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.
Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).
Pediconi, "Color-coded automated signal intensity-curve for detection and characterization of breast lesions: Preliminary evaluation of new software for MR-based breast imaging," International Congress Series 1281 (2005) 1081-1086.
Sakic et al., "Mammogram synthesis using a 3D simulation. I. breast tissue model and image acquisition simulation" Medical Physics. 29, pp. 2131-2139 (2002).
Samani, A. et al., "Biomechanical 3-D Finite Element Modeling of the Human Breast Using MRI Data", 2001, IEEE Transactions on Medical Imaging, vol. 20, No. 4, pp. 271-279.

(56) References Cited

OTHER PUBLICATIONS

Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).

Yin, H.M., et al., "Image Parser: a tool for finite element generation from three-dimensional medical images", BioMedical Engineering Online. 3:31, pp. 1-9, Oct. 1, 2004.

Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.

Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.

\* cited by examiner

Projection Image Customization Table

| # | Kv | mA | Filter | Start Time | Duration | Compression |
|---|----|----|--------|------------|----------|-------------|
| 1 |    |    |        |            |          |             |
| 2 |    |    |        |            |          |             |
| 3 |    |    |        |            |          |             |
| .. |   |    |        |            |          |             |

Figure 5

SYSTEM AND METHOD FOR DUAL ENERGY AND/OR CONTRAST ENHANCED BREAST IMAGING FOR SCREENING, DIAGNOSIS AND BIOPSY

CROSS-REFERENCE TO RELATED APPLICATIONS

This application is a continuation of U.S. patent application Ser. No. 14/695,090, filed Apr. 24, 2015, now U.S. Pat. No. 10,357,211, titled METHOD FOR DUAL ENERGY AND/OR CONTRAST ENHANCED BREAST IMAGING FOR SCREENING, DIAGNOSIS AND BIOPSY, which is a continuation U.S. patent application Ser. No. 13/415,675, filed Mar. 8, 2012, now U.S. Pat. No. 9,020,579, which claims priority under 35 U.S.C. § 119 from provisional U.S. Patent Application Ser. No. 61/450,304 filed Mar. 8, 2011, the contents of which are incorporated herein by reference. To the extent appropriate, priority is claimed to each of the above recited applications and each of the above recited applications are incorporated by reference in their entireties.

FIELD

This patent specification relates to medical imaging and more specifically to a system that enables selection among a plurality of different imaging modes, a plurality of different imaging processes, image acquisition parameters and image processing techniques.

BACKGROUND

Several references are listed at the end of the disclosure portions of this patent specification and are referred to below by numbers in parenthesis. These references a well as prior patents identified in this patent specification are hereby incorporated by reference.

In the U.S. breast cancer mortality is second only to that of lung cancer for women. Because of its role in early tumor detection, x-ray mammography has become them most commonly used tool for breast cancer screening, diagnosis and evaluation in the United States. A mammogram is an x-ray image of inner breast tissue that is used to visualize normal and abnormal structures within the breasts. Mammograms provide early cancer detection because they can often show breast lumps and/or calcifications before they are manually palpable.

While screening x-ray mammography is recognized as the most effective method for early detection of breast cancer, it also presents challenges in that in some cases it may be difficult to determine whether a detected abnormality is associated with a cancerous or benign lesion. One reason for this is that a mammogram Mp is a two dimensional projection image representing a three dimensional structure, and overlapping structures in the compressed breast may confound image interpretation and diagnosis. A second reason is that the x-rays that are often used to obtain the images have energies that are in a range that helps achieve a desirable Signal to Noise Ratio (SNR) but at the same time may cause the x-rays to be attenuated to a similar degree by breast structures that may have different clinical significance.

Efforts to improve the sensitivity and specificity of breast x-rays have included the development of breast tomosynthesis systems. Breast tomosynthesis is a three-dimensional imaging technology that involves acquiring images of a stationary compressed breast at multiple angles during a short scan. The individual projection tomosynthesis images Tp taken at respective angles of the imaging x-ray beam relative to the breast are then computer-processed into a series of reconstructed tomosinthesis slice images Tr each representing a respective slice of the breast. The Tp and/or Tr images can be displayed individually or concurrently or in a dynamic ciné mode. Breast tomosynthesis mammography [see references 14-19] typically uses a field digital mammography (FFDM) platform. In one example, an x-ray tube moves in an arc above the breast and a series of 11 to 22 low dose x-ray 2-D tomosynthesis projection images Tp is obtained. The sum of the dose from all of the 2-D tomosynthesis projection images Tp is similar to the dose from a single conventional digital mammogram Mp. These low-dose 2-D tomosynthesis projection images Tp are reconstructed into a series of 3-D slice images Tr each representing a slice of the breast where each slice is, for example, 1-5 mm thick. The slice images typically conform to planes parallel to the platform supporting the breast during image acquisition, but could be oriented differently. An advantage of breast tomosynthesis compared to conventional mammography is that by showing the breast as a series of slices rather than a single mammogram, a lesion may be seen with greater clarity because much of the superimposed tissue present in a conventional mammogram has been removed.

Reconstructed tomosynthesis slice images Tr reduce or eliminate problems caused by tissue overlap and structure noise in two-dimensional mammography imaging. Digital breast tomosynthesis also offers the possibility of reduced breast compression, improved diagnostic and screening accuracy, fewer recalls, and 3D lesion localization. An example of a multi-mode breast tomosynthesis/mammography system is described in commonly assigned U.S. Pat. No. 7,869,563. Other aspects of breast tomosynthesis and mammography are described in commonly assigned U.S. Pat. Nos. 7,991,106, 7,760,924, 7,702,142, and 7,245,694, which are hereby incorporated by reference.

In an effort to address challenges in differentiating breast cancer from benign abnormalities in breast x-ray imaging, consideration has been given to contrast-enhanced and dual-energy imaging. In contrast-enhanced imaging, a contrast agent that may be iodine-based is introduced into the breast, typically through an injection in a vein remote from the breast, and x-ray images are taken after (as well as possibly before) the contrast agent has reached the breast. The contrast agent helps highlight vascularity in the breast. If images of the same breast taken before and after the arrival of the contrast agent in the breast are subtracted from each other (and absent breast motion between the times the two images are taken), breast vascularity may be appear even more clearly in the resulting subtraction image. This may assist in differentiating cancer from benign tissue because it is believed that breast cancers release angiogenesis factors that increase the formation of small vessels near the tumor (1, 2). (The Arabic numbers in parenthesis refer to respective publications listed at the end of this patent specification.) It is believed that the growth of breast cancer is dependent on angiogenesis, and that these vessels differ from normal vessels in that they have increased permeability and are often tortuous. Imaging of the vessels around a tumor is believed to allow improved detection of breast cancer.

MRI (Magnetic Resonance Imaging) can be used with contrast enhancement to help characterize breast cancers by imaging the vascular network near a breast cancer (3). Although contrast enhanced breast MRI (CEMRI) can be effective in imaging breast cancer it has limitations including high cost, long procedure time, enhancement of benign abnormalities such as fibroadenomas, and inability to image women with metal clips or claustrophobia. Typically, the contrast agent used in CEMRI is gadolinium-based and is different from the contrast agents used in x-ray imaging.

X-ray imaging also can use contrast enhancement to improve cancer detection. The use of contrast agents such as iodine with x-ray methods has been suggested for imaging the vascular network near a breast cancer. These x-ray imaging methods include breast CT (4, 5), breast tomosynthesis (6, 7) and digital mammography (8-13). Contrast enhanced x-ray mammography (CEM) may improve the conspicuity of breast cancers (8-13). It has also been suggested that CEM may provide improved specificity compared to CEMRI because fewer benign lesions enhance (13). These studies are small and may need to be validated with larger trials.

In x-ray mammography, contrast enhanced mammography has been evaluated using two methods. The first involves subtraction of images obtained pre- and post-contrast (9). This method is referred to as time subtraction. The second method is referred to as dual-energy contrast imaging. In this method images are obtained at low energy and high energy after the injection of contrast. The images are obtained at energies above and below the k-edge of iodine (33.2 keV) when iodine-based contrast agent is used. At x-ray energies just above the k-edge the absorption of x-rays is increased resulting in an increase of contrast from the iodine contrast agent in the high energy image. Subtraction of these two images enhances iodine contrast while suppressing the contrast of normal breast anatomy. An advantage of dual-energy contrast imaging mammography is that both images may be obtained in a very short time and therefore the images may be subtracted with little patient motion. This is not true for subtraction of pre- and post-contrast images since typically there will be more than a minute separating the acquisition of the two images.

One goal of any x-ray imaging system is to obtain the highest quality images to reduce the occurrence of false positive and false negative diagnoses. It would be desirable to identify a system and method for acquiring x-ray images to alleviate issues associated with specificity and sensitivity in current designs.

SUMMARY OF THE DISCLOSURE

The patent specification describes x-ray imaging systems and methods that facilitate x-ray screening and diagnosis of patients, particularly of patients' breasts, and particularly for abnormalities characterized by suspicious vascularity. In a non-limiting example, combination of imaging modes are used, preferably in a single breast compression, to obtain a collection of x-ray images that provide unexpectedly better facility of screening and diagnosis of such abnormalities. As one example, the new system and method are used to image a patient's breast after an x-ray contrast agent has been introduced in the breast. A selected time after injecting the contrast agent, the system obtains 3D slice images representing respective slices of a patient's breast. These 3D slice images are formed by computer-processing, through a reconstruction algorithm, a multiplicity of x-ray 2D tomosynthesis projection images of the breast taken at respective angles of an imaging x-ray beam to the breast. The system also obtains a 2D combination image of a low-energy 2D x-ray mammogram and a high-energy 2D x-ray mammogram of the breast. These 2D projection images and low-energy and high-energy mammograms preferably are obtained in a single compression of the patient's breast. The system displays, preferably concurrently, the 2D combination image and one or more of the 3D slice images. The displayed combination 2D image facilitates identification of a position of a possible vascular abnormality in two dimensions, and the 3D slice images facilitate identification of the position of the abnormality in three dimensions and enables visualization of the appearance of the abnormality in respective slice images.

These and other aspects of the system and method are further explained in the detailed description that follows and in the appended drawings.

BRIEF DESCRIPTION OF THE DRAWINGS

FIG. 5 illustrates a customization table for parameters used in carrying out breast imaging.

DETAILED DESCRIPTION OF ILLUSTRATIVE EMBODIMENTS

Figure 1:
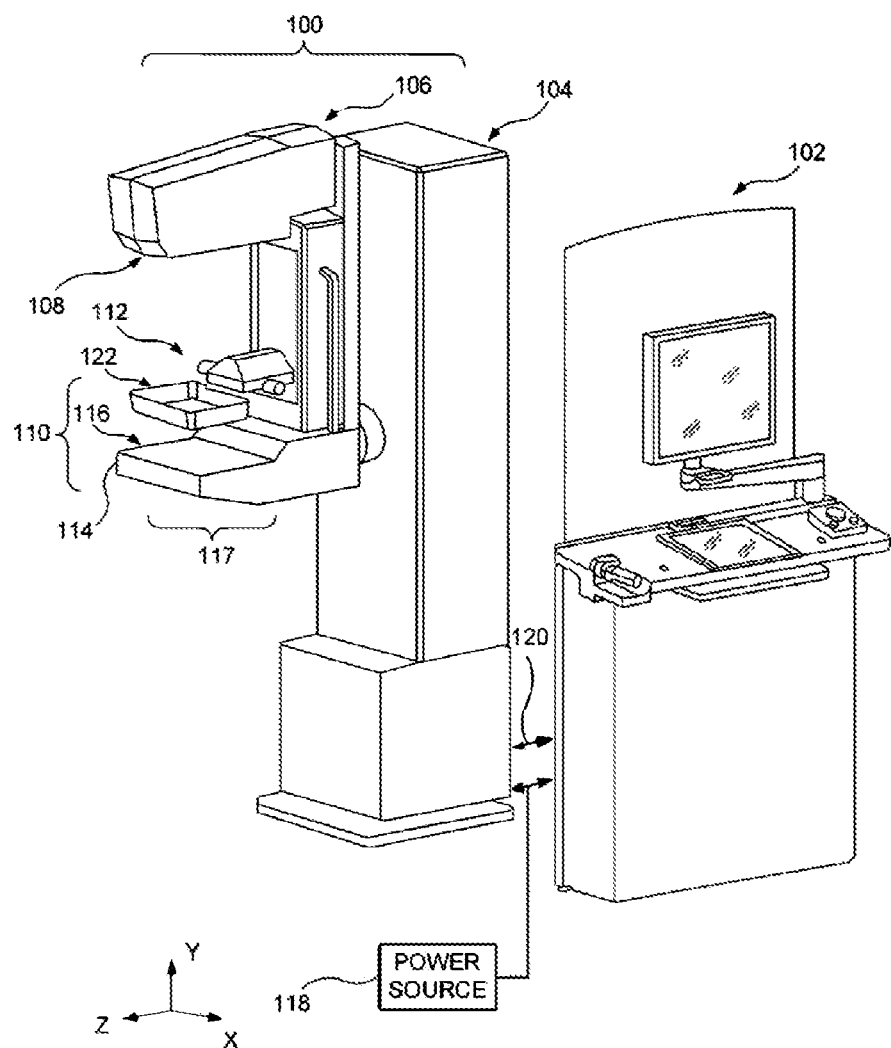
FIG. 1 illustrates an x-ray breast imaging system that provides a choice of multiple imaging modes including a 3D tomosynthesis mode and a 2D mammography mode, in each case using single-energy imaging of dual-energy imaging, and in each case with or without a contrast agent in the breast.

The examples of systems and methods described in this patent specification leverage and combine advantages of one or more image acquisition modes, including two-dimensional (2D), three-dimensional (3D), dual-energy (DE) and contrast-enhancement (CE) imaging to provide a breast imaging system with improved sensitivity and specificity and with benefits for more efficacious screening and diagnosis, greater convenience for the radiologist and better patient workflow.

A system according to one example includes an x-ray source including one or more x-ray filters, an imaging x-ray detector, and an immobilization mechanism positioned between the x-ray source and the detector for immobilizing an object to be imaged such as a patient's breast. During image acquisition, X-rays of two or more different energy ranges are generated from the x-ray source by varying at least one x-ray source acquisition parameter, including but not limited to the x-ray filters and x-ray kV. The x-rays prop to through the imaged object and are received by the detector. The composition of the imaged object modulates the x-rays through mechanisms such as attenuation, absorption and scatter, resulting in relatively brighter and darker areas in a detected image. The detected image is processed using computer-processing techniques and the resulting images may be stored and/or displayed at a radiologist's workstation.

The system may include a control module for controlling image acquisition, the control module including a user interface permitting a user to select one or more modes of image acquisition and/or image processing. The user interface may comprise a key pad, touch pad, joystick or other input mechanism that interacts with a computer program executing on a computer system coupled to a display. Such a user interface may enable selection of image acquisition mode, such as a 2D mammography mode, a 3D tomosynthesis imaging mode or a combination 2D/3D imaging mode depending upon the capabilities of the breast imaging device.

Alternatively (or in combination) the interface may enable further customization of image acquisition via selection of particular acquisition parameters and acquisition processes within each selected imaging mode. For example, the system is adapted to implement a dual-energy image acquisition process for at least one image acquired in 2D, 3D or a combination (combo) mode. In addition, the system ay be configured to perform a background subtraction image acquisition process for images acquired in dual-energy 2D, 3D and/or combo modes.

In addition to enabling the selection of various imaging processes within each image mode, the system may be configured to enable a user to customize the acquisition parameters of a given mode or process. Thus the system may further allow the user to identify acquisition parameters such as contrast agent, kV, mA, image timing, and x-ray filter type. As will be described in more detail later herein, the selection of parameters may be varied between different 2D image acquisitions, such as between sequential projection images Tp during a tomosynthesis acquisition, and to trigger imaging in relation to the timing of introducing a contrast agent.

In addition to enabling selection of acquisition modes and operating parameters, the user interface may allow selection of various forms of image processing that are to be used on the captured image, including a 3D reconstruction process (backward projection, forward projection, with weighting, etc.), noise filtering algorithms, subtraction of different energy images with or without differential weighting, addition of different energy images with or without differential weighting, etc. Alternatively, the control module may be programmed to select a preferred method of image processing in accordance with a selected acquisition mode, or in accordance with a selected operating parameter, or a combination thereof.

These and other features will now be described in greater detail with regard to the figures.

Image Acquisition

One example is an x-ray image acquisition system that is optimized for mammography and breast tomosynthesis and is further modified for dual-energy imaging and for the use of a contrast agent. One system that can serve as a basis for further modifications is the Selenia® Dimensions® tomosynthesis imaging system, manufactured and sold by Hologic, Inc., of Bedford Mass. This system is a combo-mode system capable of acquiring images in either or both 2D and 3D mode, but it should be clear that this is not the only example of a suitable system, that tomosynthesis-only systems also may serve as a basis for modification, and that some aspects of mammography-only systems also may be useful as a basis for further modifications. Accordingly, the systems and methods described in this patent specification are not limited to a particular starting system that can be used or modified to carry out the required processes. Certain aspects of examples of a starting system are described in the commonly owned patents cited above.

Figure 2:
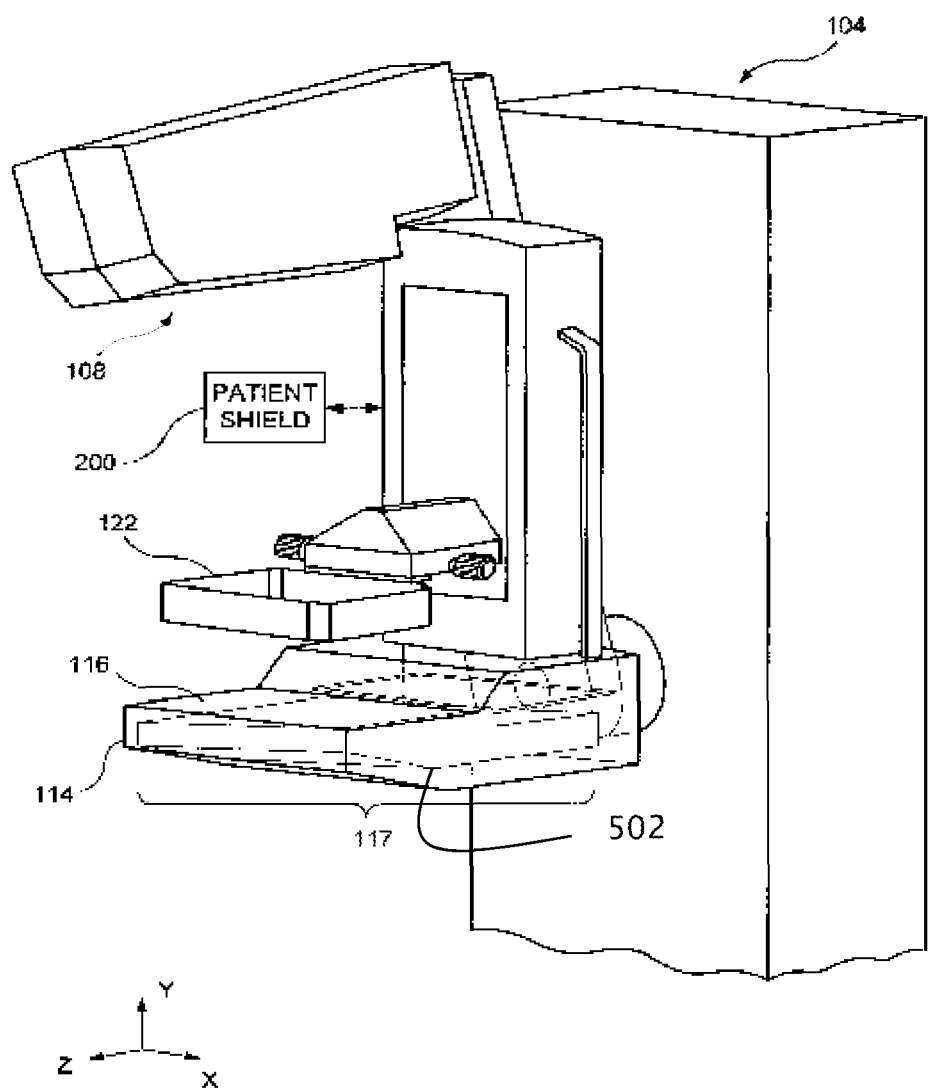
FIG. 2 illustrates in greater detail a portion of the FIG. 1 system.
Figure 3:
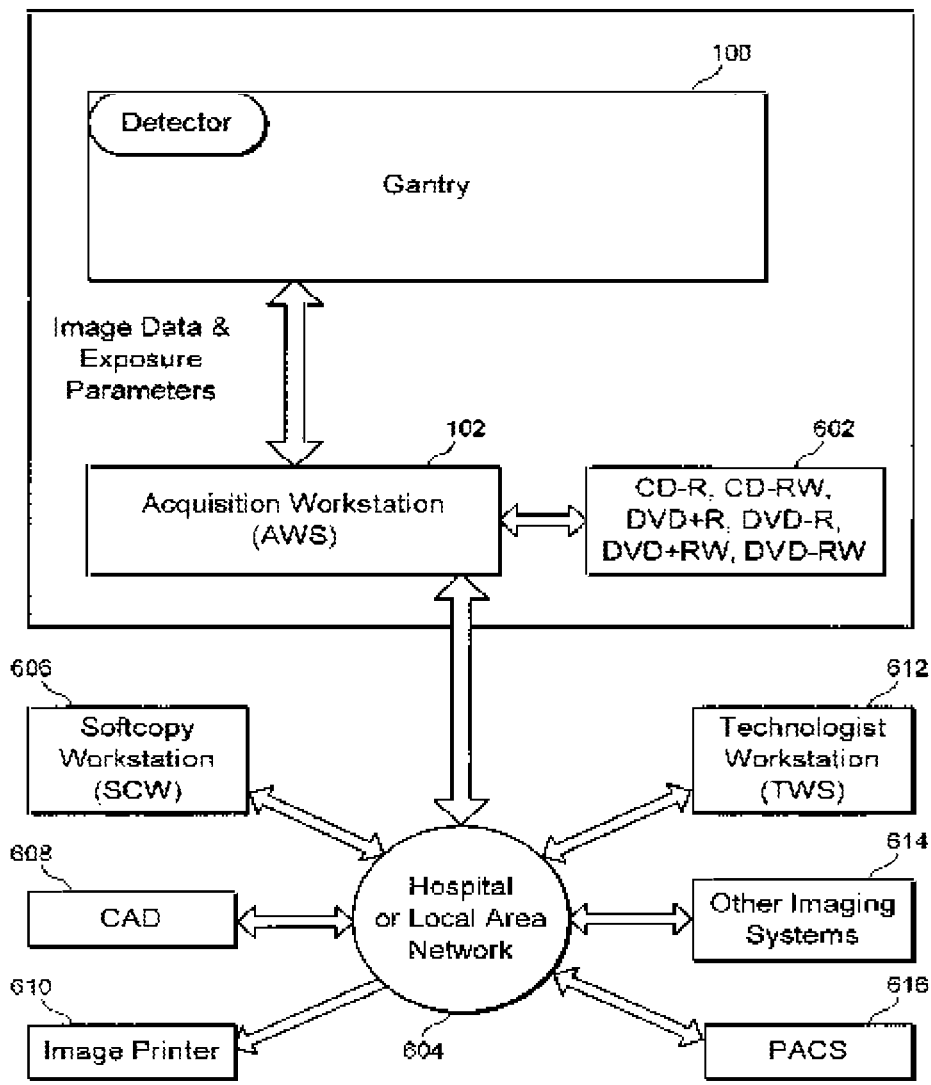
FIG. 3 illustrates further aspects of the FIG. 1 system.

FIGS. 1-3 illustrate various components of a non-limiting example of a multi-mode mammography/tomosynthesis system that can carry out the processes described in this patent specification with suitable additions or modification for dual-energy imaging described below. The system comprises a gantry 100 and a data acquisition work-station 102. Gantry 100 includes a housing 104 supporting a tube arm assembly 106 rotatably mounted thereon to pivot about a horizontal axis 402 and carrying an x-ray tube assembly 108. X-ray tube assembly 108 includes (1) an x-ray tube generating x-ray energy in a selected range, such as 20-50 kV, at mAs such as in the range 3-400 mAs, with focal spots such as a nominal size 0.3 mm large spot and nominal size 0.1 mm small spot (2) supports for multiple x-ray filters such as molybdenum, rhodium, aluminum, copper, cesium iodide, silver and tin filters, and (3) an adjustable collimation assembly selectively collimating the x-ray beam from the focal spot in a range such as from a 7 by 8 cm rectangle to a 24 by 29 cm rectangle when measured at the image plane of an x-ray image receptor 502 included in the system, at a maximum source-image distance such as 75 cm. Also mounted on housing 104, for rotation about the same axis 402 (or a different axis), is a compression arm assembly 110 that comprises a compression plate or paddle 122 and a receptor housing 114 having an upper surface 116 serving as a breast plate or platform and enclosing an image detector subsystem system 117 comprising a flat panel x-ray imaging receptor 502 (FIG. 2), a retractable anti-scatter grid, and a mechanism for driving and retracting anti-scatter grid between a position in which the imaging x-ray beam passes through the grid and a position in which the grid is outside the imaging x-ray beam. Housing 104 also encloses a vertical travel assembly 404 for moving tube arm assembly 106 and compression arm assembly 110 up and down to accommodate a particular patient or imaging position, a tube arm assembly rotation mechanism to rotate tube arm assembly 106 about the horizontal axis for different imaging positions, a detector subsystem rotation mechanism for rotating components of detector subsystem 117 about the horizontal axis to accommodate different operations modes, and a couple/uncouple mechanism to selectively couple or uncouple tube arm assembly 106 and compression arm assembly 110 to and from each other, and tube arm assembly 106 and detector subsystem 117 to and from each other. Housing 104 also encloses suitable motors and electrical and mechanical components and connections to implement the functions discussed here. A patient shield 200, schematically illustrated in FIG. 2, can be secured to compression arm assembly 110 to provide a mechanical interlock against patient contact with the rotating x-ray tube arm assembly 106. Work-station 102 comprises components similar to those in the Selenia® mammography system and in the Selenia® Dimension® combo system, including a display screen (typically a flat panel display that may include touch-screen functionality), user interface devices such as a keyboard, possibly a touch-screen, and a mouse or trackball, and various switches and indicator lights and/or displays. Work-station 102 also includes computer facilities similar to those of the Selenia® and the Selenia® Dimensions® system (but adapted through hardware, firmware and software differences) for controlling gantry 100 and for processing, storing and displaying data received from gantry 100. A power generation facility for x-ray tube assembly 108 may be included in housing 104 or in work-station 102. A power source 118 powers work-station 102. Gantry 100 and work-station 102 exchange data and controls over a schematically illustrated connection 120.

As illustrated in FIG. 3, additional storage facilities 602 can be connected to work-station 102, such as one or more optical disc drives for storing information such as images and/or for providing information to work-station 102 such as previously obtained images and software, or a local printer (not shown). In addition, the disclosed system can be connected to a hospital or local area or other network 604, and through the network to other systems such as a soft copy workstation 606, a CAD (Computer Aided Detection) station 608 for computer-processing mammography and/or tomosynthesis images to identify likely abnormalities, an image printer 610 for printing images, a technologist workstation 612, other imaging systems 614 such as other mammography systems or systems for other modalities for exchange of images and/or other information, and to a PACS (Picture Archiving) systems 616 for archiving images and other information and/or retrieving images and other information.

In standard mammography mode, typically used for screening mammography, tube arm assembly 106 and compression arm assembly 110 are coupled and locked together in a relative position such as seen in FIG. 1, such that an x-ray beam from x-ray tube assembly 108 illuminates x-ray receptor 502 when the patient's breast is compressed by compression device 112. In this mode, the system operates in a manner similar to said Selenia® system to take a mammogram. Vertical travel assembly 404 and tube arm rotation mechanism can make vertical adjustments to accommodate a patient, and can rotate tube arm assembly 106 and compression arm assembly 110 together as a unit about the horizontal axis for different image orientations such as for CC and for MLO images. For example, tube arm assembly 106 and compression arm assembly 110 can rotate between (−195.degree.) and (+150.degree.) about the axis. As in the Selenia® system, compression device 112 includes a compression paddle 122 that can move laterally, in a direction along the chest wall of a patient, to adjust for different imaging orientations. The compression paddle may comprise any one of a plurality of types of paddles, including but not limited to a full paddle, a spot paddle, or a curved paddle (which may be preferred for use in contrast image acquisition processes described below), and may be configured to tilt against a spring bias and/or to move laterally, as described in the commonly owned patents identified above.

In tomosynthesis mode, as used for example in said Selenia® Dimensions® system and as described in said U.S. Pat. No. 7,869,563, tube arm assembly 106 and compression arm assembly 110 are decoupled such that compression arm assembly 110 stays in one position, compressing the patient's breast, while tube arm assembly 106 rotates about the horizontal axis, for example +/−15 degrees relative to compression arm assembly 110. Tomosynthesis can be carried out for different image orientations, so that compression arm assembly 110 can be rotated about the horizontal axis (alone or together with assembly 106) for a desired image orientation and locked in place, and then tube arm assembly 106 can be rotated relative to that position of compression arm assembly 110 for tomosynthesis imaging over +/−15 degree or some other desired angular range. For example, low dose tomosynthesis may be performed over a seven degree angular range to collect in the area of seven projection images.

In a combination mode, during a single compression of the patient's breast the system takes a conventional mammogram and tomosynthesis images. In this mode, while the breast remains compressed in compression arm assembly 110, (1) tube arm assembly 106 sweeps and x-ray receptor 502 rocks, each through an appropriate angle, and x-ray exposures are taken for tomosynthesis images, and (2) a standard mammogram is taken. The standard mammogram can be taken at a 0 (zero) degree angle relative angle between tube arm assembly 106 and a normal to the imaging plane of x-ray receptor 502, and can be taken before or after the tomosynthesis images are taken or between the taking of two successive tomosynthesis images. Typically, each tomosynthesis image utilizes substantially lower x-ray dose than the standard mammogram.

For example, as described above, the total dosage of all projection images taken during the tomosynthesis scan can range from 0.25 to 2.0 times that of the dose of a single mammogram. The relationship between the two dosages can be user-selected to control any one of the x-ray tube voltage, current, tomosynthesis scan angle, number of projection images obtained, etc. In alternate embodiments, the dosage may be altered via a simple switch on the gantry, or through a user control at a radiologist workstation. In still alternate embodiments the dosage may vary automatically as the radiologist switches between modes.

Image Acquisition Process Selection

One important characteristic of any digital imaging system is the ability to vary the amount and intensity of radiation used to generate any image. Radiation intensity is related to the atomic number (Z) of the x-ray target, the x-ray current (mA), x-ray voltage and x-ray beam filtration. Radiation intensity is varied to improve image quality, which in turn can improve diagnostic sensitivity. When radiation intensity increases, quantum mottle (image noise caused by photon absorption) tends to decrease and vice versa.

Many mammography and tomosynthesis systems allow the operator to control x-ray exposure by manually setting technique factors such as mA and mSec. Some systems include an Automatic Exposure Control (AEC) functionality which controls a duration of administration of radiation, turning off the x-ray source when the desired dose has been administered. Automatic Exposure Control (AEC) methods may vary the dosing parameters, including exposure time, kV, mA and filter modes for an image to vary the exposure and the radiation intensity.

While such control over acquisition parameters may provide some improvement over image quality, according to one aspect of the system and method described in this patent specification, improved image quality may be provided by incorporating additional acquisition processes into 2D, 3D or combo systems to realize the benefits of contrast image enhancement according to new approaches described in this patent specification.

A breast imaging system according to examples described in this patent specification combines the capabilities of combined 2D and/or 3D breast x-ray imaging with benefits from contrast image acquisition processes. Biopsy capability (stereotactic or tomosynthesis guided) may also be integrated into the system, with lesion localization software utilizing any images selected from a group including simple 2D images, 3D projection images, 3D reconstructed data, or any of the 2D, 3D projection and 3D reconstructed data obtained during a dual energy or background subtraction image acquisition process.

With such arrangements, the following image protocols are supported:

Contrast imaging (background subtraction) using a single high or low energy image acquisition technique, in 2D or 3D mode.

Dual-energy contrast imaging in 2D or 3D mode;

Dual-energy contrast imaging in 3D mode, wherein high and low energy exposures occur at different angles during a tomosynthesis scan; [high and low energies can be reconstructed separately and combined to form the dual energy volume];

Dual-energy imaging in a combo system that acquires dual-energy 2D and dual-energy 3D images;

In combo imaging mode, where the 2D image data set is acquired using a single energy, and the 3D image data set is acquired using dual-energy imaging;

In combo imaging mode, where the 2D image data set is acquired using dual-energy imaging, and the 3D image data set is acquired using a single energy image;

Tomosynthesis imaging mode, wherein among a total of N views in a contrast tomo scan wherein the breast remains n compression throughout the scan, different projection images are allotted different dose, kVps, mAs and filters for greater flexibility of different applications;

Tomosynthesis mode wherein a low energy scans and high energy scans alternate in a series f acquired projection images;

Tomosynthesis mode wherein low energy and high energy scans are performed for the projection images, in unequal ratios in user selectable patterns;

Stereotactic biopsy using contrast agent, and either dual energy or background subtraction imaging;

Upright biopsy using tomosynthesis scan images obtained using a contrast agent and either dual-energy or background subtraction imaging;

Other variations of combinations of contrast imaging and image acquisition modes are within the scope of this patent specification.

Image Acquisition Parameter Selection

Once an image acquisition mode and an acquisition process are identified, acquisition parameters and image processing techniques can be varied at a projection image granularity by varying at least one of kV, mA and/or filter for each 2D image capture.

Several modifications to existing mammography and/or tomosynthesis breast imaging systems may be made to support contrast imaging. For example, within the x-ray source, mechanisms that allow fast switching between kV, mA and x-ray beam filters may be provided to support dual-energy imaging between and within image capture modes. For example, an x-ray filter wheel may be provided to switch filters between low and high energy pulses. A variety of different filters, such as rhodium, silver, aluminum, copper and cesium iodide may be provided to provide the desired energy for different contrast agents.

Figure 3A:
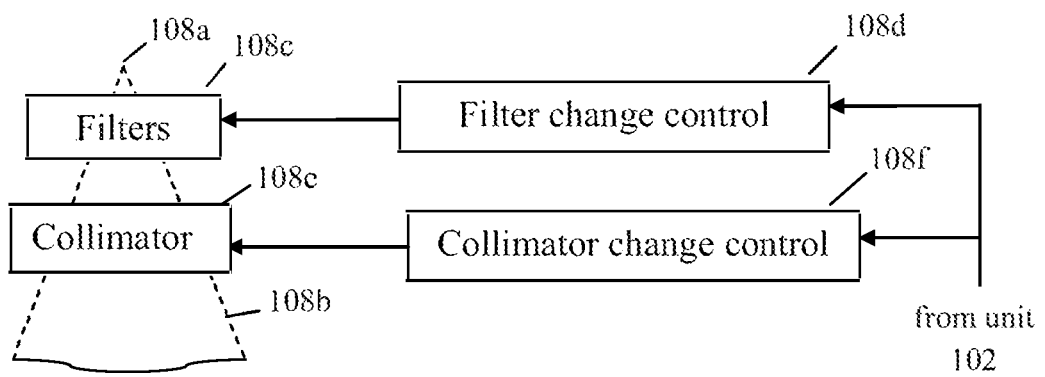
FIG. 3a illustrates an example of a variable filter/collimator mechanism.

FIG. 3a schematically illustrates an example where a focal spot 108a inside x-ray source 108 emits an imaging x-ray beam 108b toward an imaging x-ray receptor. The beam passes through a variable filter assembly 108c that contains a mechanism for interposing a selected filter in the beam path to thereby control the energy range of the x-rays that continue toward the imaging receptor. A filter change control 108d determines which filter will intercept the x-ray beam, and in turn is controlled by system settings or by a user through unit 102. Variable filter arrangement are known in the field, as they are used in a variety of systems, including dual energy bone densitometry systems of the type offered by the common assignee. A variable collimator 108e controls the area of the x-ray imaging beam at the imaging plane of the receptor, and is in turn controlled by a collimator controller 108f that can also receive commands from unit 102.

Figure 4:
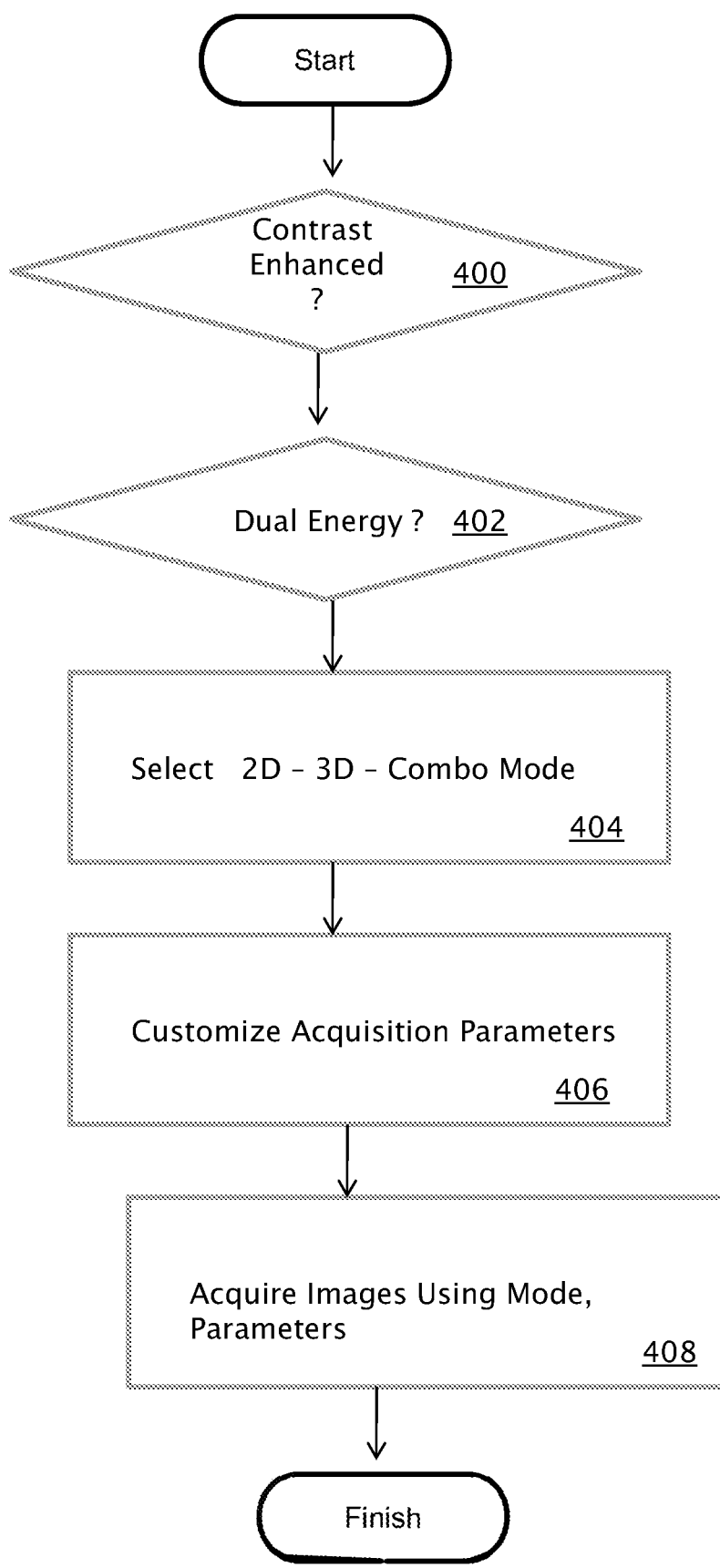
FIG. 4 illustrates steps in an example of operation of a breast imaging system.

The new systems described in this patent specification allow users to select physical acquisition parameters at a projection image granularity. For example, FIG. 4 illustrates an example of process steps that can be followed. In step 400 a decision is made whether to set the system to operate in a contrast-enhanced mode and in step 402 a decision is made whether to operate the system in a dual-energy mode. These decisions can be made by a user, or can be made automatically by the system depending on some information that a user enters. In step 404 the user or the system selects whether to operate in 2D mode only, in 3D mode only, or in a combination of 2D and 3D modes. In step 406, the system or the user may customize acquisition parameters such as kV, mAs, etc., and in step 408 the system operates with the settings selected in steps 400-406 to acquire images Tp and/or Mp.

FIG. 5 illustrates an example of a tomosynthesis projection image customization table that may be presented to the user for manual customization of images of a tomosynthesis scan. Although certain fields are shown in the table, this patent specification anticipates that any acquisition variable may be made available to a user for customization of the image in this manner. Such a table may initially be populated with default values, which may be system defaults or default values populated following analysis of image data received in response to AEC, or may be filled in by a user and entered into the system.

Image Processing Selection

The new system also allows different image processing to be performed on received images, where the image processing techniques may be determined in response to a type of acquisition (i.e., a tomosynthesis acquisition, a 2D acquisition, a dual-energy acquisition, a contrast acquisition). Thus, for example, images acquired using high energy may be processed using different algorithms than images acquired using low energy. The image processing technique may be preprogrammed based on the selected acquisition mode or alternatively may be selected in response to user input. For the purposes of this patent specification, image processing refers to any manipulation and combination of the images, including noise filtering and image reconstruction. Some of the processing may be a function of the acquisition mode. For example, when performing background subtraction contrast imaging using tomosynthesis images, pre and post injection projection images may be subtracted, and the resulting signal shifted to register the images to compensate for patient motion.

In one embodiment, the new system enables the utilization of either gain controlled images or air-map corrected images as a basis for the contrast image processes (i.e., the images may be processed prior to the subtraction or addition processes). Gain controlled images are images that have been processed to compensate for system gain to increase SNR, for example using techniques described in said commonly assigned U.S. Pat. No. 7,991,106.

Display

A display of the new system may be used to display images captured using any of the modalities (2D, 3D, combo), using any image acquisition process. The display includes the ability to display the images in a variety of configurations, including singularly, side by side, toggled, or in cine-mode. With such an arrangement, a health professional may simultaneously view (or toggle between, or view in cine), the 2D image, 3D projection image or 3D slice image of a breast, at either the low energy acquisition, high energy acquisition, or following subtraction of the two, with or without the use of contrast agents, thereby enhancing the ability to visualize and characterize lesions.

Figure 6B:
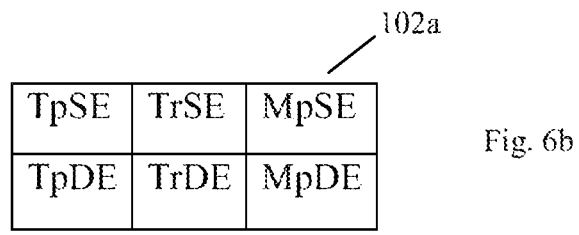
FIG. 6a illustrated a display of images taken in different aging modes of a system such as that illustrated in FIG. 2, FIG. 6b schematically illustrates a display of ages taken in six different imaging modes of a system such as that of FIG. 1.
Figure 6A:
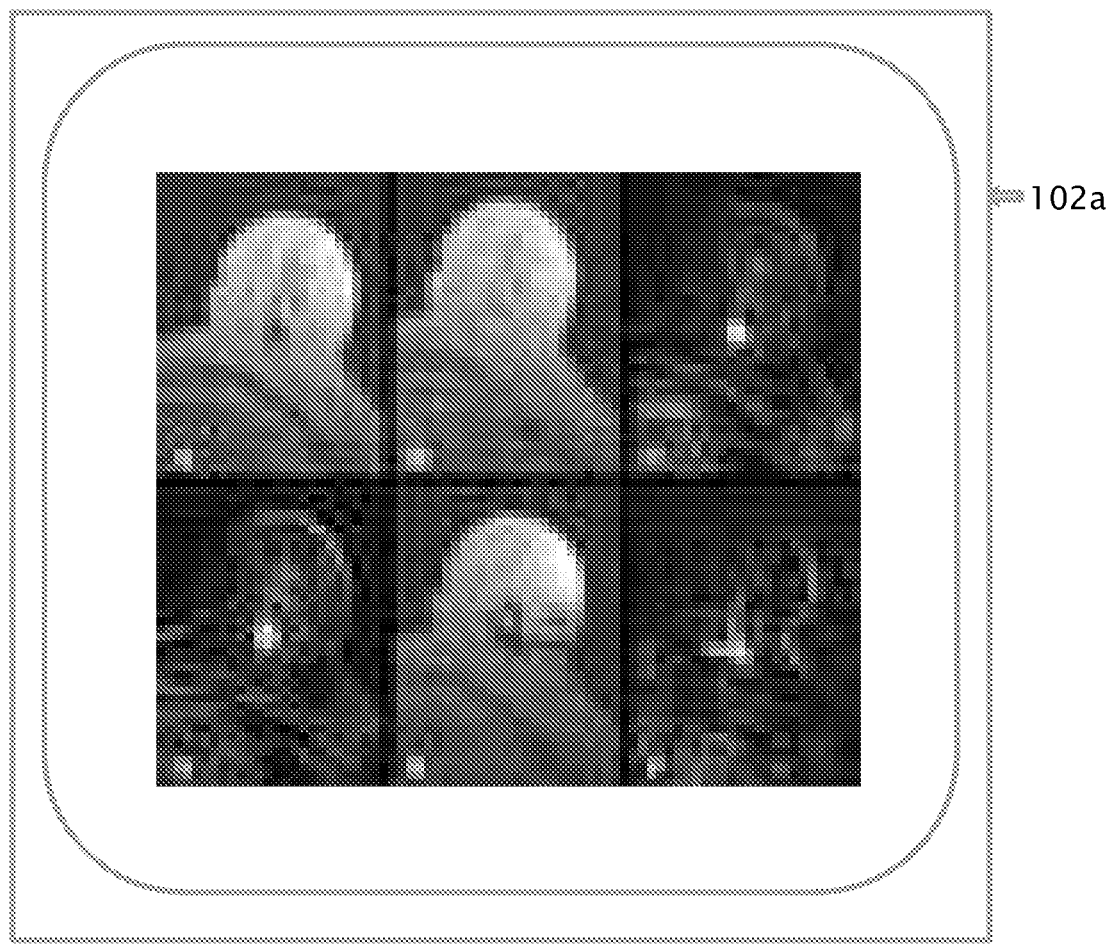

FIG. 6a illustrates an example in which different types of images are presented side-by-side, in respective windows of a computer display 102a. FIG. 6b schematically illustrates an example of computer display 102a that concurrently shows six different images of a patient's breast: a single-energy tomosynthesis projection image TpSE, a single-energy reconstructed tomosynthesis slice image TrSE, a single-energy mammogram MpSE, a dual-energy tomosynthesis projection image TpDE, a dual-energy reconstructed tomosynthesis slice image TrDE, and a dual-energy mammogram MpDE, It should be understood that in this context the term single-energy refers to the range of energies that an x-ray tube emits at a particular parameter setting of parameters that determine x-ray the energies that the tube emits, and the term dual energy refers to two such energy ranges that may partly overlap. It should also be understood that FIG. 6b illustrates one of the many examples of arranging images according to this patent specification, and that the image display may show only a subset of the illustrated images, may show images in a different relative arrangement, may show multiple images of the same kind (e.g., multiple images Tp, etc.), may show superimposed images, and/or may show images in cine mode, and may show a single image over the entire screen or may divide the screen into a different number of windows.

Figure 7:
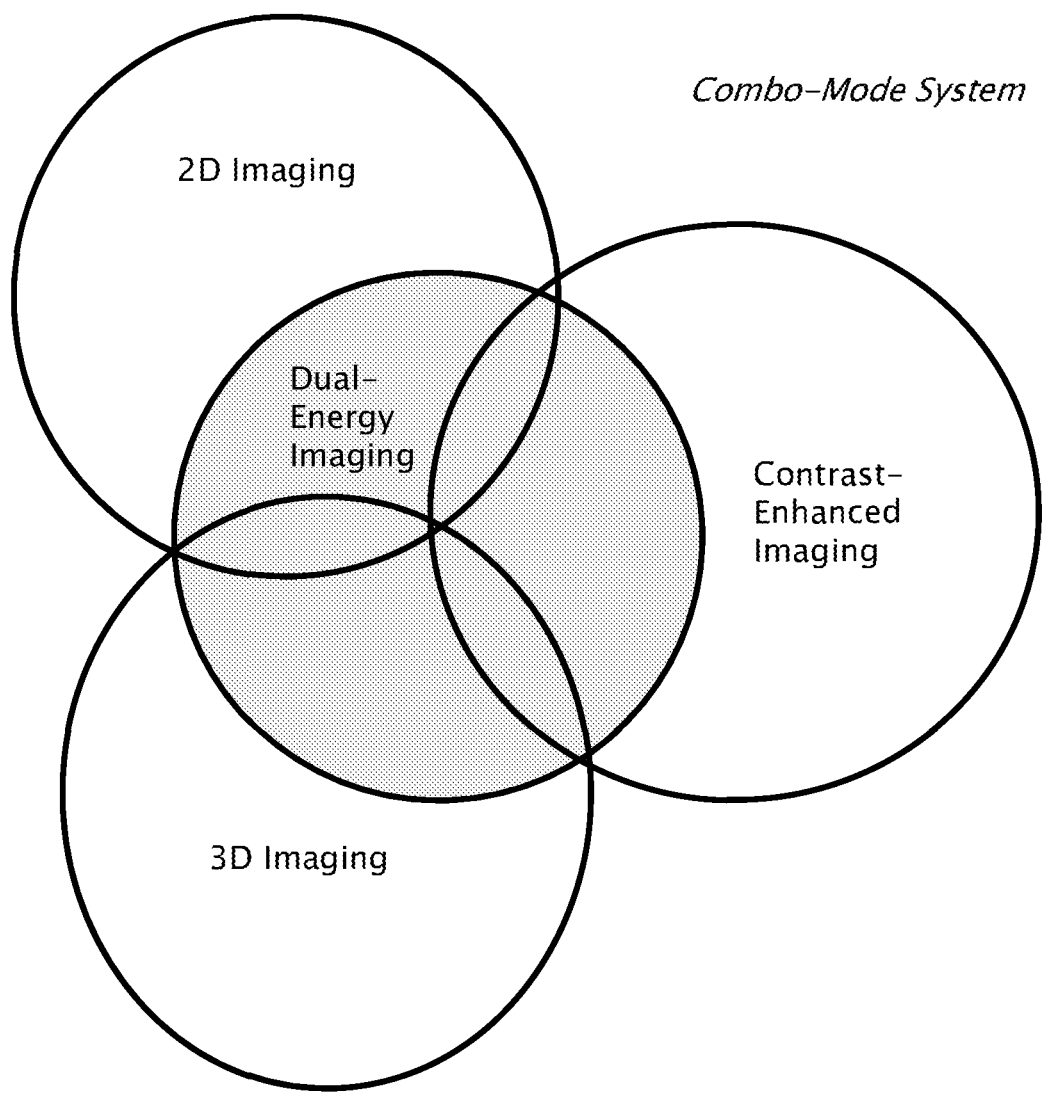
FIG. 7 illustrates possible combinations of imaging modes of a system such as illustrated in FIG. 1.
Figure 8:
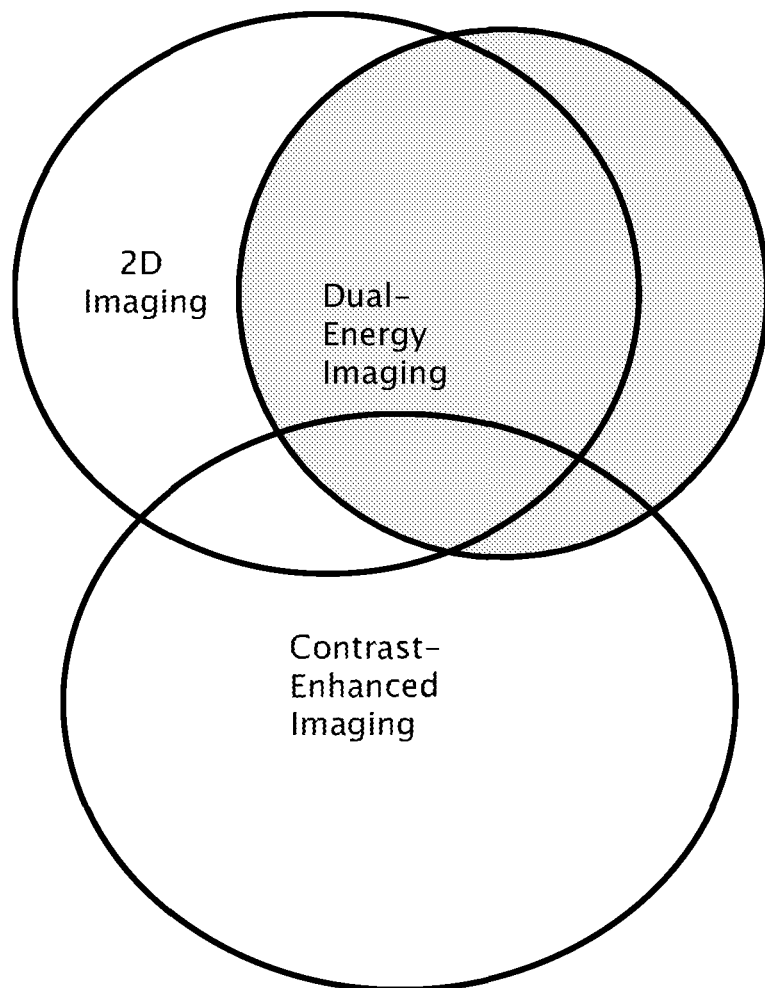
FIG. 8 is a similar illustration of possible combinations of imaging modes in a system that takes only 2D images.
Figure 9:
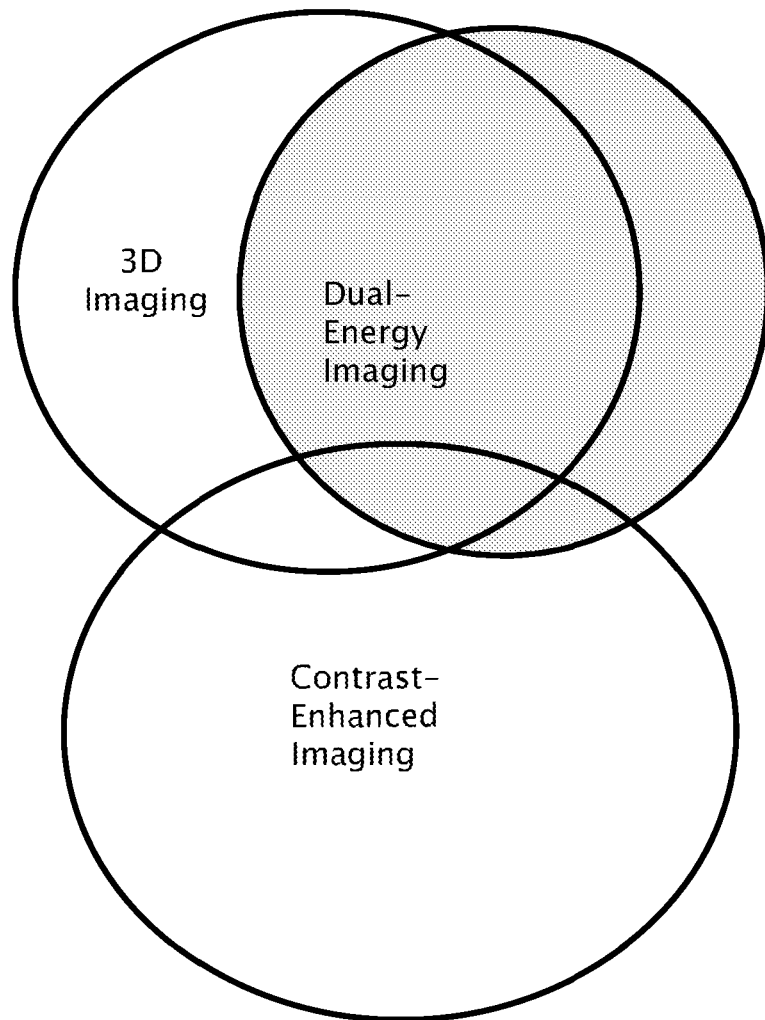
FIG. 9 is a similar illustration of possible combinations of imaging modes in a system that takes only 3D images.

FIG. 7 illustrates a scope of imaging in different modes of operation, of a combo system that operates in either or both of a 2D imaging mammography mode and a 3D imaging tomosynthesis mode. In each of these 2D and 3D modes, the system can operate image the breast with or without contrast agent in the breast. In either or both of the 2D and 3D modes, and with or without contrast agent in the breast, the system can carry out dual-energy imaging or background subtraction imaging. As seen in FIG. 7, these capabilities allow for many different combinations of modes such as 2D using single-energy (SE) and contrast enhancement (CE), 2D using SE, 3D using CE, 3D using DE, etc. FIG. 8 illustrates a scope of imaging when using a 2D only system, i.e., a system that does not include 3D tomosynthesis capabilities. In the FIG. 8 example, the system can be used in single-energy or dual-energy modes, in each case with or without contrast agent in the breast. FIG. 9 illustrates the operation of a 3D only system that can operate in 3D imaging mode using single-energy or dual-energy imaging, in either case with or without contrast agent in the breast.

Although the above has described the use of the new system with regard to acquisition of both tomosynthesis and mammogram images, this patent specification is not limited to an integrated multi-mode system but applies to any system that is capable of performing tomosynthesis. For example the new system may include only tomosynthesis imaging capability. Such systems may use a legacy mammogram for example for calcification detection, or may obtain a single tomosynthesis image at higher dosage to use as their 2D image, or may synthesize a mammogram image from tomosynthesis projection images. In addition, the new system may incorporate tomosynthesis imaging capability with a different modality, such as molecular breast imaging or ultrasound imaging. In short any breast imaging systems which includes tomosynthesis imaging capabilities falls within the scope of this patent specification. Still in addition, some of the improvements described in this patent specification also apply to systems that take only 2D images.

The above specific examples and embodiments are illustrative, and many variations can be introduced on these examples and embodiments without departing from the spirit of the disclosure or from the scope of the appended claims. For example, elements and/or features of different illustrative embodiments may be combined with each other and/or substituted for each other within the scope of this disclosure and appended claims.

Preferred Examples

In a preferred example, the system described in this patent specification obtains (i) 3D tomosynthesis slice images TrSE of a patient's breast that represent respective slices of the breast and are reconstructed through computer-processing of a multiplicity of single-energy x-ray 2D tomosynthesis projection images TpSE of the patient's breast, (ii) a low-energy x-ray 2D mammogram MpL, and (ii) a high-energy x-ray 2D mammogram MpH of the breast. The Tp, MpL and MpH images preferably are taken in a single breast compression, while the breast remains immobilized. The system computer-processes the 2D low-energy mammogram MpL and the 2D high-energy mammogram MpH to form a weighted combination dual-energy 2D mammogram image MpCDE that tends to highlight vascularity in the breast. The system displays, preferably concurrently, (i) the combination 2D image MpCDE, which can help reveals positions of possible vascular abnormalities in two dimensions, and (ii) 3D slice images TrSE in which the abnormalities appear and which can help reveal 3D positions of the abnormalities and the appearance of the abnormalities in the slice images.

Preferably, the system is configured to respond to an identification of an abnormality in the MpCDE image to automatically identify the subset of TrSE images in which the abnormality appears. Also preferably, the system is configured to concurrently display the MpCDE image and either one or more but not all of the images of said subset of TrSE images, or the entire subset.

Figure 10:
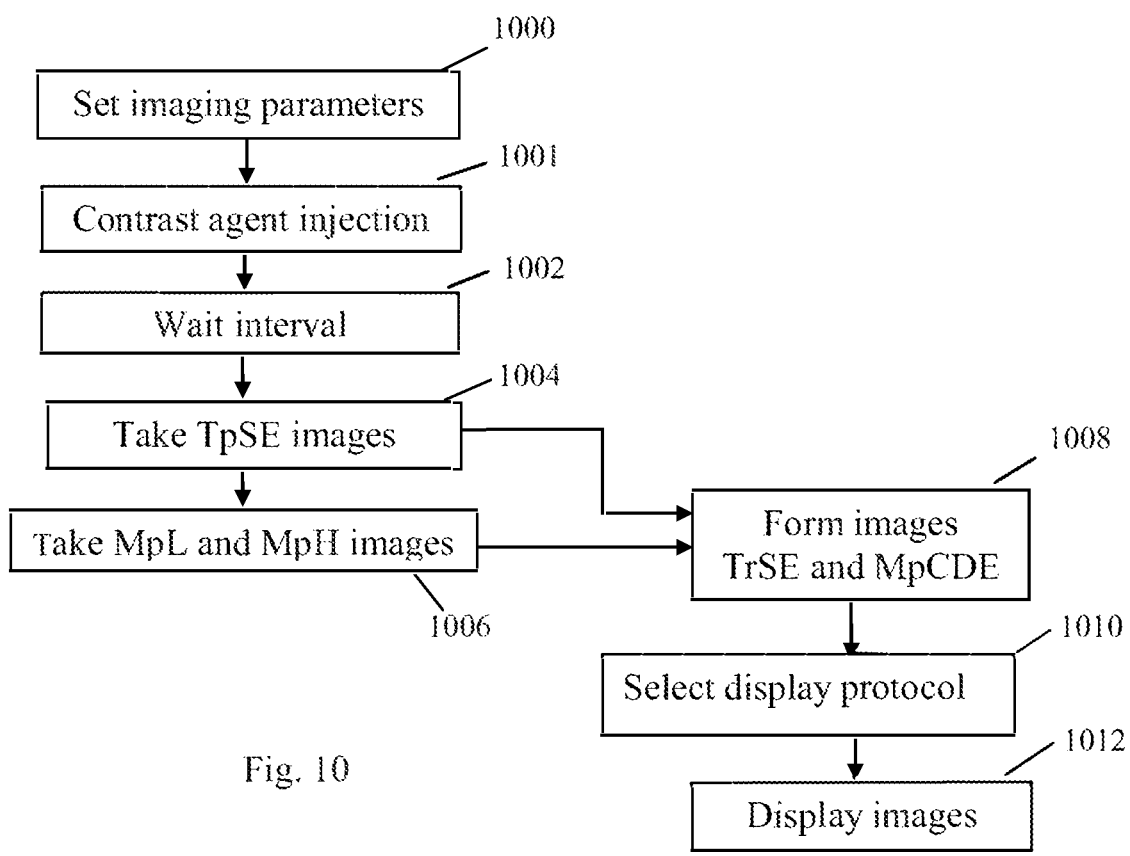
FIG. 10 illustrates steps in a preferred example of operation of a system such as illustrated in FIG. 1.

FIG. 10 illustrates steps of a method for carrying out imaging according to the preferred example. In step 1000, imaging parameters such as those illustrated in FIG. 4 are set for an imaging sequence. This can be done either by storing a default in the system, e.g., in acquisition workstation 102 shown in FIG. 1, or more typically by selecting parameters adapted to a particular patient and/or a particular study, using for example a table such as illustrated in FIG. 5. In step 1001, a contrast agent is injected, such as a standard FDA-approved low osmolarity Iodine contrast agent. In one example, 350-370 mg/ml of the contrast agent are injected at a rate of 3 to 3.5 ml/sec, or within safety parameters of the IV gauge in place, with a total volume of 1.5 ml/kg patient weight up to a maximum of 150 ml. In general, the agent can be the same as commonly used clinically for contrast-enhanced CT scanning of the chest and abdomen. The injection can be in the antecubital or forearm vein. Step 1002 is waiting time, typically of the order of a minute or two after the start of the injection. The duration of step 1002 is set based on health professionals' assessment of the time needed for the contrast agent to reach a desirable concentration in the breast. In step 1004, the patient's breast is compressed in the manner known for tomosynthesis images and a system such as that illustrated in FIG. 1, or such as the Selenia® Dimensions® available from the assignee, operates in a single-energy tomosynthesis mode to take plural single-energy projection images TpSE of the breast, for example 22 images TpSE, each from a respective different angle of the imaging x-ray beam relative to the breast, over an angular range such as ±15°. In step 1006 and while the patient's breast remains compressed and immobilized, the system takes a low-energy mammogram MpL and a high-energy mammogram MpH, for example by returning the x-ray source to a 0° position and taking the image MpL with one x-ray filter in the imaging x-ray beam, then changing to a different x-ray filter and taking the image MpH. Preferably, x-ray energies in the 30-40 kVp range are used for the TrSE images, less than 35 kVp (e.g., in the 28-30 kVp range) for the MpL image, and more than 45 kVp (e.g., in the 45-49 kVp range) for the MpH image. However, different energies can be used in a manner consistent with clinical practice. As one example, a Rhodium or Silver x-ray filter can be used for the MpL image but a Copper filter for the MpH image. The other imaging parameters follow typical clinical practice and may depend on factors such as the thickness and x-ray density of the compressed breast.

In step 1008, the TpSE images are computer-processed to form TrSE images, using reconstruction algorithms of the type described in the material incorporated by reference, and the MpL and MpH images are computer-processed to form a combined image MpCDE. For example, the combined image is obtained according to the relationship MpCDE=MpH−kMpL, where k is a weighting factor and typically k>1, as is known in the dual-energy x-ray imaging technology. In step 1010, a display protocol is selected, either automatically according to a preset default protocol or as selected by a user for a particular patient study or a particular display, and can be set into a workstation such as unit 102 of FIG. 1 or into a separate imaging workstation. In step 1012 one or more of the images TrSE and MpCDE are displayed on a screen such as screen 102a shown in FIG. 6b. In addition, other images can be displayed on the same screen or other screens, such as any of the images TpSE and other images such as images of the breast obtained at other times with the same or different modalities such as, without limitation, MRI, CT, nuclear medicine imaging devices, and ultrasound Numerous variations are possible in the order of steps illustrated in FIG. 10. For example, the order of steps 1004 and 1006 can be reversed, Step 108 can start before step 1006, or well after step 1006. Steps 1008, 1010 and 1012 can be carried out in devices remote from unit 100 illustrated in FIG. 1.

It should be appreciated that the preferred example illustrated above is only one of many examples consistent with this patent specification, and that other combination of modes and steps also are within the scope of the specification

The invention claimed is:

1. A method for imaging a breast of a patient, the method comprising:
 compressing, between an x-ray source and an x-ray detector, the breast of the patient for a single compression;
 injecting a first contrast agent into the breast of the patient
  subsequent to injecting the first contrast agent, emitting, from the x-ray source, a first x-ray beam at a first x-ray energy and a second x-ray beam at a second energy less than the first x-ray energy;
 detecting, by the x-ray detector, the first x-ray beam and the second x-ray beam after the first x-ray beam and the second x-ray beam have passed through the breast;
 based on the detected first x-ray beam and second x-ray beam, generating a first 2D mammography image;
 receiving an image acquisition mode selection;
 emitting, from the x-ray source, a plurality of third x-ray beams at a third x-ray energy, wherein the third x-ray energy is different from the first x-ray energy and the second x-ray energy, and wherein the plurality of third x-ray beams are emitted from at least two different locations relative to the compressed breast of the patient;
 detecting, by the x-ray detector, the plurality of third x-ray beams after the third x-ray beams have passed through the breast;
 based on the received image acquisition mode selection and the detected plurality of third x-ray beams, generating, by a processor, either of a tomosynthesis image or a second 2D mammography image;
 based on the received image acquisition mode selection, displaying either of the tomosynthesis image or the second 2D mammography image;
 localizing a lesion of the breast within the displayed either of the tomosynthesis image or the second 2D mammography image; and
 subsequent to localizing the lesion, releasing the breast of the patient from the single compression.

2. The method of claim 1, wherein localizing the lesion includes performing, by the processor, computer aided detection.

3. The method of claim 1, wherein localizing the lesion is performed as part of a stereotactic or tomosynthesis guided biopsy procedure.

4. The method of claim 1, wherein the second 2D mammography image is further based on a background subtraction imaging acquisition process.

5. The method of claim 1, wherein at least one of the first 2D mammography image and the second 2D mammography image comprises at least one of a subtraction 2D mammography image and a low energy 2D mammography image.

6. A system for imaging a breast of a patient, the system comprising:
 an x-ray source capable of selectively moving relative to a patient's breast;
 an imaging x-ray detector;
 a compression mechanism disposed between the x-ray source and the imaging x-ray detector;
 a control module programmed with a set of instructions that when executed cause the system to perform a set of operations, comprising:
  compressing, between the x-ray source and the x-ray detector, the breast of the patient for a single compression;
  injecting a first contrast agent into the breast of the patient;
  subsequent to injecting the first contrast agent, emitting, from the x-ray source, a first x-ray beam at a first x-ray energy and a second x-ray beam at a second energy less than the first x-ray energy;
  detecting, by the x-ray detector, the first x-ray beam and the second x-ray beam after the first x-ray beam and the second x-ray beam have passed through the breast;

based on the detected first x-ray beam and second x-ray beam, generating a first 2D mammography image;

receiving an image acquisition mode selection;

emitting, from the x-ray source, a plurality of third x-ray beams at a third x-ray energy, wherein the third x-ray energy is different from the first x-ray energy and the second x-ray energy, and wherein the plurality of third x-ray beams are emitted from at least two different locations relative to the compressed breast of the patient;

detecting, by the x-ray detector, the plurality of third x-ray beams after the third x-ray beams have passed through the breast;

based on the received image acquisition mode selection and the detected plurality of third x-ray beams, generating, by a processor operatively connected to the x-ray detector, either of a tomosynthesis image or a second 2D mammography image;

based on the received image acquisition mode selection, displaying either of the tomosynthesis image or the second 2D mammography image;

localizing a lesion of the breast within the displayed either of the tomosynthesis image or the second 2D mammography image; and subsequent to localizing the lesion, releasing the breast of the patient from the single compression.

7. The system of claim 6, wherein localizing the lesion includes performing computer aided detection.

8. The system of claim 6, wherein localizing the lesion is performed as part of a stereotactic or tomosynthesis guided biopsy procedure.

9. The system of claim 6, wherein the second 2D mammography image is further based on a background subtraction imaging acquisition process.

10. The method of claim 6, wherein at least one of the first 2D mammography image and the second 2D mammography image comprises at least one of a subtraction 2D mammography image and a low energy 2D mammography image.

11. A method for imaging a breast of a patient, the method comprising:

compressing the breast, for a single compression, between an x-ray source and an x-ray detector;

injecting a first contrast agent into the breast of the patient;

subsequent to injecting the first contrast agent, emitting, from the x-ray source, a first x-ray beam at a first x-ray energy;

detecting, by the x-ray detector, the first x-ray beam;

emitting, from the x-ray source, a second x-ray beam at a second x-ray energy, wherein the second x-ray energy is different from the first x-ray energy;

detecting, by the x-ray detector, the second x-ray beam;

generating a first 2D mammography image from the detected first x-ray beam and the second x-ray beam;

receiving an image acquisition mode selection;

emitting, from the x-ray source, a plurality of third x-ray beams at a third x-ray energy, wherein the third x-ray energy is different from the first x-ray energy and the second x-ray energy, and wherein the plurality of third x-ray beams are emitted from at least two different locations relative to the compressed breast of the patient;

detecting, by the x-ray detector, the plurality of third x-ray beams after the third x-ray beams have passed through the breast;

based on the received image acquisition mode selection and the detected plurality of third x-ray beams, generating, by a processor, either of a tomosynthesis slice image or a second 2D mammography image;

based on the received image acquisition mode selection, displaying either of the second 2D mammogram image or the tomosynthesis slice image;

localizing an abnormality of the breast within the displayed second 2D mammogram image or the displayed tomosynthesis slice image; and subsequent to localizing the abnormality, releasing the breast of the patient from the single compression.

12. The method of claim 11, wherein the second 2D mammogram image and the tomosynthesis slice image are displayed concurrently.

13. The method of claim 11, further comprising moving the x-ray source relative to the breast.

14. The method of claim 11, wherein localizing the abnormality includes performing computer aided detection.

15. The method of claim 11, wherein localizing the abnormality is performed as part of a stereotactic or tomosynthesis guided biopsy procedure.

16. The method of claim 11, wherein at least one of the first 2D mammography image and the second 2D mammography image comprises at least one of a subtraction 2D mammography image and a low energy 2D mammography image.

* * * * *